| United States Patent [19] | [11] Patent Number: 4,817,432 |
|---|---|
| Wallace et al. | [45] Date of Patent: Apr. 4, 1989 |

[54] DIGITAL ULTRASONIC INSTRUMENT FOR OPHTHALMIC USE

[75] Inventors: David A. Wallace, Beverly Hills; Steven E. Feldon, San Marino; Gary Mezack, Norco; Douglas L. Whiting, South Pasadena; William J. Dally, Pasadena; Scott A. Karns, Pomona, all of Calif.

[73] Assignee: Design Team Partners, Glendale, Calif.

[21] Appl. No.: 781,257

[22] Filed: Sep. 27, 1985

[51] Int. Cl.⁴ ............................................. G01N 29/04
[52] U.S. Cl. .................................. 73/602; 128/661.06
[58] Field of Search .................. 73/602, 629; 128/660; 364/563

[56] References Cited

U.S. PATENT DOCUMENTS

| 4,398,420 | 8/1983 | Haesen et al. | 364/563 |
| 4,412,248 | 10/1983 | Carmen | 73/602 |
| 4,564,018 | 1/1986 | Hutchison et al. | 128/660 |

*Primary Examiner*—Stewart J. Levy
*Assistant Examiner*—Louis M. Arana
*Attorney, Agent, or Firm*—Lyon & Lyon

[57] ABSTRACT

Disclosed is a digital ultrasonic instrument for measuring the corneal thickness (often referred to as a pachymeter) and for measuring the axial length of the eye (often referred to as a biometric ruler). A number representing corneal thickness or axial length is displayed digitally on a liquid crystal display. The pachymeter incorporates a 20 MHz solid phase piezoelectric transducer, a microprocessor, a gate array, a hybrid analog receiver circuit, a liquid crystal display and four batteries. When axial length is measured, the instrument operates as a biometric ruler, a 10 MHz transducer is used and the software in the microprocessor is modified. Ultrasonic echoes generated by the transducer and various interfaces in the eye are sampled at the rate of 40 MHz which results in equal or greater sensitivity, resolution and accuracy as compared to other pachymeters and biometric rulers currently available. The 40 MHz sample rate is accomplished by use of a grey code counter and a binary counter, each of which is sampled twice after an ultrasonic echo is detected. The two grey code samples are compared to determine a valid sample period. A counter value obtained during a valid sample period is recorded in a shift register and compared to subsequent counter values corresponding to subsequent ultrasonic echoes. The apparatus for correlating ultrasonic echoes with particular counter values assures that the counter will be sampled at a point in time when the counter is stable as opposed to being in a state of transition. The apparatus allows for a counter accuracy of 25 ns.

3 Claims, 5 Drawing Sheets

| BINARY STATE | G1:G0 | BINARY B1:B0 |
|---|---|---|
| 3 | 0 0 | 1 1 |
| 0 | 0 1 | 0 0 |
| 1 | 1 1 | 0 1 |
| 2 | 1 0 | 1 0 |
| 3 | 0 0 | 1 1 |

FIG. 8b

```
132  9-BIT CNTR CLOCK   ________----------------________-
134  BINARY STATE          3  :  0  :  1  :  2  :  3  :
136  9-BIT CNTR OUTPUT  ________XXXXXXXX________
```

FIG. 9

| P1 SAMPLE G1:G0 STATE | P2 SAMPLE G1:G0 STATE | 8-BIT SAMPLE SELECTION | VALID STATE |
|---|---|---|---|
| 3 | 3 | P1 | 3 |
| 3 | 0 | P1 | 3 |
| 3 | 1 | P3 | 0 |
| 0 | 0 | P3 | 0 |
| 0 | 1 | P3 | 0 |
| 0 | 2 | P3 | 1 |
| 1 | 1 | P3 | 1 |
| 1 | 2 | P3 | 1 |
| 1 | 3 | P1 | 2 |
| 2 | 2 | P1 | 2 |
| 2 | 3 | P1 | 2 |
| 2 | 0 | P1 | 3 |

DIGITAL ULTRASONIC INSTRUMENT FOR OPHTHALMIC USE

BACKGROUND OF THE INVENTION

In the field of ophthalmology, myopia (near-sightedness) is the most common optical refractive error. In recent years this condition has been corrected through procedures such as radial keratotomy (RK). In this surgery, a series of radial incisions of precise depth are placed in the cornea, effecting a change in its curvature and hence its refractive power. The length and number of incisions required in an RK operation varies according to the degree of optical correction desired, and the depth of the incision is critical to the satisfactory outcome of the surgery. Inadequate depth will result in under-correction, whereas excessive depth will result in over-correction or perforation of the cornea and potentially serious harm to the eye. Accurate measurement of the corneal thickness is therefore essential to the safe and successful performance of RK surgery.

Instruments that measure corneal thickness are referred to as pachymeters. Early pachymeters were purely optical devices and have been shown to be imprecise. Ultrasonic technology is now routinely used to measure corneal thickness. All current instruments employ an ultrasonic probe that contacts the eye and which is attached via a cable to a desk unit which is about the size of an oscilloscope. Some units have a small oscilloscope screen that displays the transducer tracings and other more recent units simply display a digital readout of the corneal thickness on the device. The speed at which the echoes are sampled determines the accuracy with which the thickness measurement can be made. CMOS digital devices cannot reliably run an 11-bit synchronous counter system at 40 MHz using current semiconductor technology. It would therefore be useful to devise a CMOS based system that sampled ultrasonic echoes at frequencies in the 40 MHz range in order to achieve greater sensitivity, resolution and accuracy of measurement.

The most commonly performed operation in ophthalmology is cataract surgery. A cataract is an opacification of the biological lens inside the eye. In cataract extraction, one of several techniques is used to remove the opacified lens material. Once removed, it is possible to implant an artificial lens in order to restore optical integrity to the eye, eliminating the need for thick cataract glasses or contact lenses.

When cataract surgery is performed, several measurements are necessary in order to calculate the precise power of the intraocular lens (IOL) to be implanted. The important variables are corneal curvature (keratometry), size of the eye (axial length), and knowledge of where inside the eye the IOL is to be implanted (anterior or posterior chamber). Measurement of axial length is performed ultrasonically by a device referred to as a biometric ruler. Through such an instrument, the major internal structures of the eye can be imaged and their dimensions measured. Of importance in the measurement of true axial length is the distance from the cornea to the retina along the visual axis of the eye. The early biometric rulers employed a piezoelectric transducer, in a hand-held probe attached via a cable to an oscilloscope. It was necessary for the individual performing the examination to visually assess the oscilloscope signals and identify an axial scan. Second generation instruments still require the examiner to detect the pattern consistent with an axial scan. Then, electronics are used to calculate and display the desired measurement in millimeters. It would be desirable to have a portable, digital, ultrasonic biometric ruler for displaying the axial length of the eye, using microprocessor technology to assess the echo waveforms and displaying digitally a readout representing as accurately as possible the true axial length of the eye.

CROSS REFERENCE TO RELATED APPLICATIONS

The present invention is related to the apparatus disclosed in the application entitled "Self-Contained Hand-Held Ultrasonic Instrument for Ophthalmic Use" filed concurrently herewith in the names of Steven E. Feldon, M.D. and David A. Wallace, M.D. with Ser. No. 781,148 and incorporated herein by reference. The present invention is also related to the apparatus disclosed in the application entitled "Hand-Held Self-Contained Electrical Tonometer" filed concurrently herewith in the names of David A. Wallace, M.D., Steven E. Feldon, M.D., Robert A. Monsour and Gary P. Mezack with Ser. No. 781,240, now U.S. Pat. No. 4,747,296 and incorporated herein by reference.

SUMMARY OF THE INVENTION

The present invention relates to a completely portable digital ultrasonic instrument for measuring corneal thickness (pachymeter) or axial length (biometric ruler) of the eye. For the pachymeter, corneal thickness is displayed digitally on a liquid crystal display (LCD). The pachymeter incorporates a 20 MHz solid phase piezoelectric transducer, a microprocessor, a gate array, a hybrid analog receiver, a liquid crystal display and four batteries. For the biometric ruler, axial length is measured using a 10 MHz transducer and the software in the microprocessor is modified. A small pinjack connector is available to link the unit to other electronic devices such as a microcomputer, personal computer or printer. The ultrasonic echoes generated by the transducer and various interfaces in the eye are sampled at the rate of 40 MHz which results in equal or greater sensitivity, resolution and accuracy as compared to other ultrasonic units currently available. The 40 MHz sample rate achieves a resolution of 25 ns. Since it is not possible to reliably run an 11-bit synchronous counter at 40 MHz using current CMOS technology, a 2-bit grey code counter running at 40 MHz is used to clock a 9-bit synchronous counter. After an echo is detected, three successive measurement times are generated. A grey code counter is sampled during the first two sample periods and the 9-bit synchronous counter is sampled during the first and third sample periods. By comparing the values of the two grey code samples, the appropriate 9-bit sample can be selected for comparison to subsequent samples which occur as a result of subsequently detected ultrasonic echoes. Using this technique insures that the selected 9-bit sample does not occur when the 9-bit synchronous counter is in a state of transition. The apparatus allows for high speed, high accuracy measurement of the time between asynchronous ultrasonic echoes which translates into highly accurate thickness measurements necessary in the field of ophthalmology.

If a 10 MHz solid phased piezoelectric transducer is substituted for the 20 MHz transducer, and the microprocessor program is changed, then the instrument can be operated as a biometric ruler for measurement of the dimensions of the major internal structures of the eye as well as measurement of the true axial length which is the distance from the cornea to the retina along the visual axis of the eye. In this mode, a pinjack connector also allows the biometric ruler unit to be attached to an oscilloscope which in turn displays the ultrasonic echoes as they occur.

It is therefore an object of the present invention to accomplish high speed, high accuracy measurement of the time between two asynchronous events.

It is a further object of the present invention to insure that the high speed sampling of a counter, after an asynchronous event has occurred, is accurate to within 25 ns when compared with a subsequent asynchronous event.

BRIEF DESCRIPTION OF THE DRAWINGS

FIG. 7 is a timing diagram illustrating the desired operation of the block diagram of FIG. 6.

DETAILED DESCRIPTION OF THE PREFERRED EMBODIMENT

Figure 1:
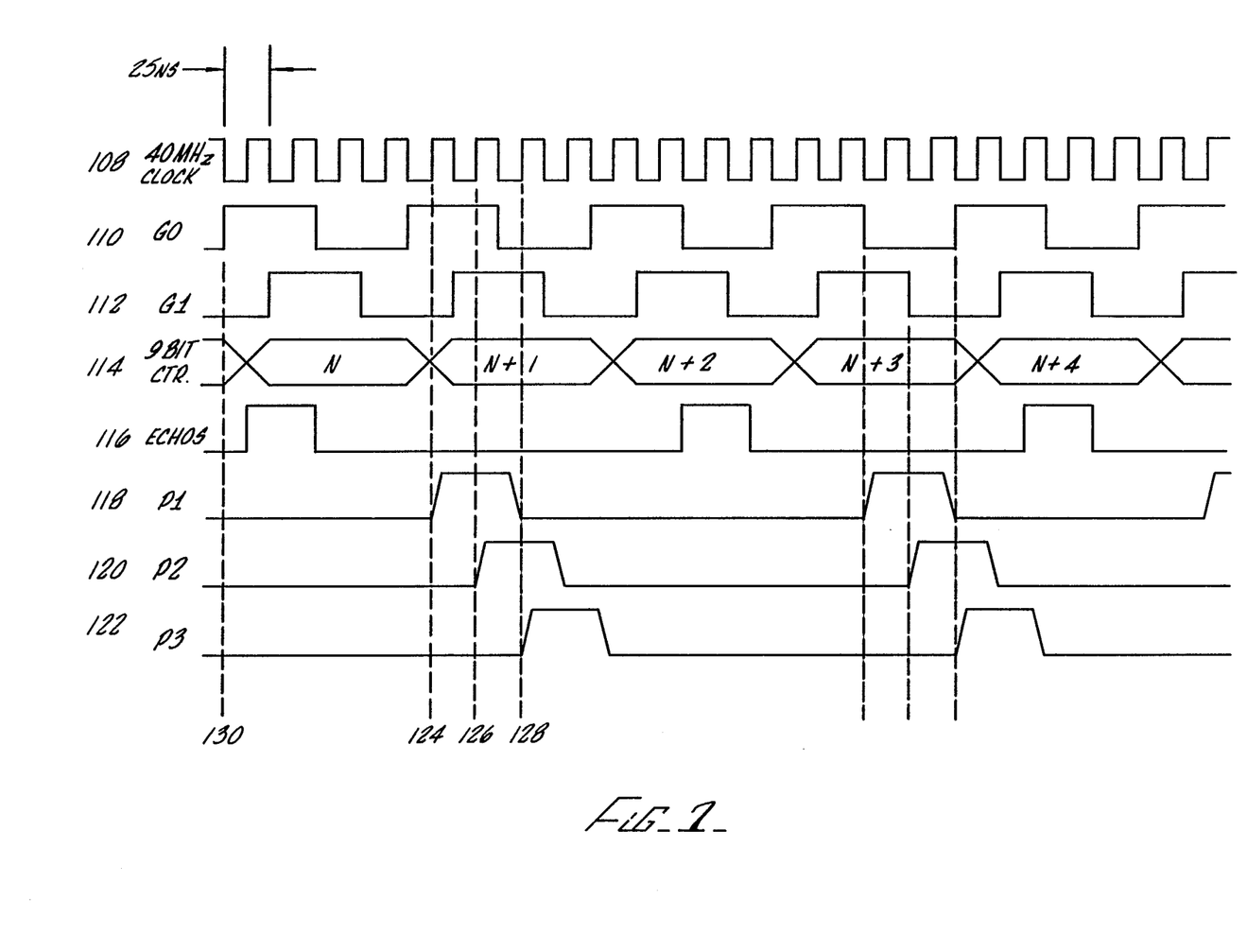
FIG. 1A is a prospective view of the instrument as a pachymeter with a 20 MHz transducer and FIG. 1B shows the biometric ruler with a 10 MHz transducer.
Figures 1A, 1B, 2A:
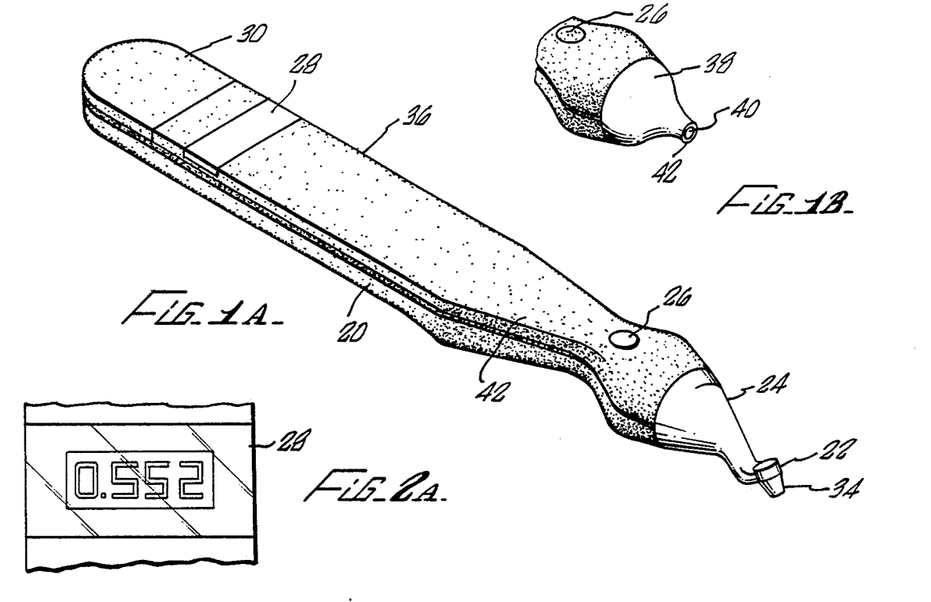
FIG. 2A shows a digital display for use with a 20 MHz transducer and FIG. 2B shows a digital display for use with a 10 MHz transducer.
Figure 4:
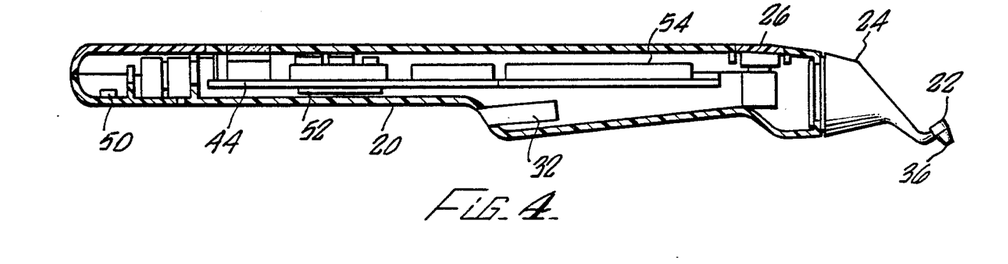
FIG. 4 is a side view of the pachymeter showing the various locations of the component parts.

Referring to FIG. 1A, the instruments comprises a housing 20 which is contoured such that it can be easily grasped in the manner of a writing pen. The tip of the instrument is a piezoelectric ultrasonic transducer element 22 mounted to a swan neck connector 24. The other functioning components of the instrument include an activation button 26, located on the anterior dorsal surface in close approximation to the index fingertip of the user, a liquid crystal display 28 (LCD), a reset button (not shown), a removable battery cover 30, and a pinjack connector 32 (FIG. 4).

The 20 MHz transducer 22 comprises a plastic ultrasonically transparent, contact head 34, and a recessed piezoelectric ultrasonic transducer 22. This cone shaped contact head 34 is attached to the transducer 22 which is attached to the swan neck connector 24 which connects to the housing 20 of the pachymeter 36. The backing of the transducer 22 is a 0.005 inch piece of tungsten-loaded epoxy which is an acoustically inert material. The piezoelectric transducer element has a frequency of 20 MHz. It is activated by means of a hybrid transceiver, which is connected to a microprocessor via a gate array. One to three pulses of current are delivered to the transducer from the hybrid transceiver. A first echo corresponds to the front corneal surface and a second echo corresponds to the back corneal surface. The time between the two corneal echoes is proportional to the corneal thickness. Because sound is estimated to travel at a rate of 1640 meters/sec through corneal tissue, the time between the emitted signal and the reflected echoes can be converted to millimeters, using standard formulae.

The active transducer element is opaque and is centered at the posterior edge of the cone shaped contact head 34. The contact head is made of a clear acrylic material that allows the instrument tip to be better visualized under an operating microscope. The small size of the transducer 22 and the contact head 34 minimizes the area of the corneal surface which is obscured by the transducer 22. In addition, the swan neck connector 24 is designed such that it is rather easy for the user to place the contact head 34 into contact with the corneal surface perpendicularly while viewing the eye under an operating microscope. In essence, the combined clear acrylic contact head 34 and the swan neck connector 24 both facilitate perpendicular alignment of the transducer 22 to the corneal surface. The transducer must be aligned perpendicular to the corneal surface in order to obtain detectable echoes from the inner corneal surface adjacent to the aqueous humor. In addition, the shortest echographic distance corresponds to the actual corneal thickness. Being slightly off perpendicular to the visual axis would result in spurious readings being obtained.

To calibrate the pachymeter with a 20 MHz transducer, an acrylic multistepped calibration block, which simulates the corneal interfaces, is placed on a flat surface. The pachymeter 36 is then held perpendicularly to the surface of the block and the activation switch 26 is pressed once and then released. A beeper and miniature speaker provide a series of clicks followed by a beep. The pachymeter reading from the surface will be displayed on the LCD display 28. This output should be within 0.01 mm of the calibration block measurement printed on its surface.

When the instrument is used as a biometric ruler, the same housing 20 is used. The tip of the instrument is a 10 MHz piezoelectric ultrasonic transducer element (not shown) mounted within a standoff 38 as shown in FIG. 1B. A special acoustically mismatched damping material is utilized to prevent "ringing" of the ultrasonic transducer which might preclude interpretation or detection of early echoes. Other functional components of the instrument include an activation button 26 located on the anterior dorsal surface in the close approximation to the index fingertip of the user, a liquid crystal display 28, a reset button (not shown) and a removable battery cover 30. The transducer head 42 is a focusing element with a focal length of 24 millimeters, corresponding to an area near the retina of the eye. The diameter of the focusing element is 0.3 inch. In the center of the focusing element is a light-emitting diode 40. The patient is asked to look at the light-emitting diode 40, which has been activated, as the probe is placed in contact with the corneal surface. This allows the patient to center the eye on the transducer, facilitating axial measurements.

In the biometric ruler, damping of the transducer "ring" is provided by 0.005 inch acoustically mismatched material (not shown) such as tungsten-loaded epoxy. The transducer element has a frequency of 10 MHz. It is activated by means of a hybrid transceiver which connects to a microprocessor via a gate array. The average speed of sound through the eye is approximately at 1560 meters per second. The time between the emitted signal, corresponding to the corneal surface, and reflected echoes are then converted into millimeters using standard formulae. One to three pulses of current are delivered to activate the transducer. After sending out the ultrasonic signal, the transducer is switched to a detection mode. The first echo corresponds to the transducer-corneal interface. All subsequent echoes are measured relative to this. The second echo, found within a "window" of 1.5 to 5 millimeters from the corneal surface, corresponds to the anterior lenticular surface. The third echo, falling into a window of 1.5 to 6.5 millimeters behind the anterior lenticular echo, corresponds to the posterior lenticular surface. The fourth echo, located 18.5 to 29.0 millimeters behind the corneal surface echo, corresponds to the retinal surface. The fifth echo, 0.29 to 2.5 millimeter behind the retina, corresponds to the scleral surface. Echoes which occur outside the given windows will be ignored.

The 10 MHz transducer is calibrated by use of an acrylic block with multiple interfaces which simulates a standardized eye. This is placed on a flat surface and the transducer head 42 is then held perpendicular to the surface of the block and the activation switch 26 is pressed once and then released. A series of clicks will sound, following which there will be a beep. The biometric ruler reading from this source will be demonstrated on the display 28. This output should be within 0.1 millimeters of the calibration block measurement printed on its surface.

Figures 2B, 3:
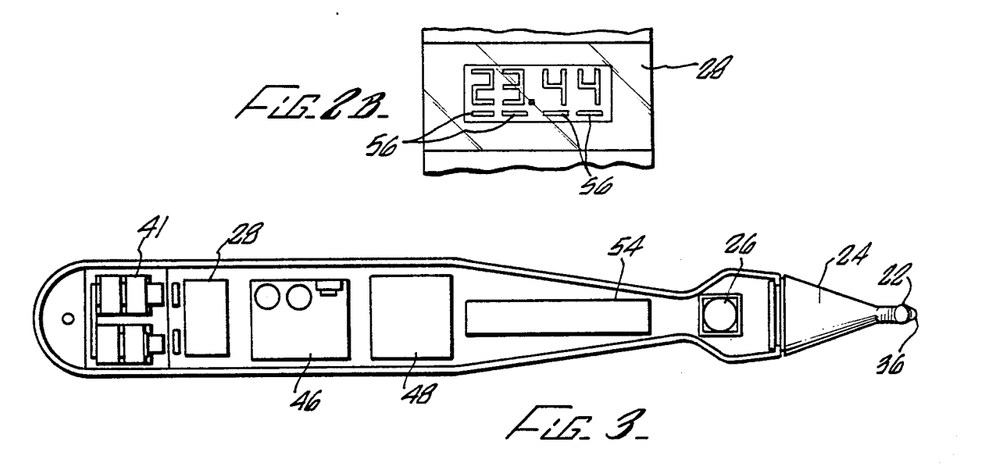
FIG. 3 shows a top view of the pachymeter with the top cover removed.

FIG. 2A shows typical information that is displayed on the digital readout 28 when the 20 MHz transducer is used and FIG. 2B shows typical information displayed when the 10 MHz transducer is substituted for the 20 MHz transducer of FIG. 1A.

FIG. 3 shows a top view of the instrument with the top cover 42 (FIG. 1A) removed. The batteries 42 are located to the rear of the instrument. The liquid crystal display 28 is connected to a circuit board 44 (FIG. 4) and is located adjacent to the microprocessor 46. A gate array 48 is located on the same circuit board 44 between the microprocessor 46 and a hybrid transceiver 54. The activation switch 26 is located between the hybrid transceiver 54 and the connector 24. The total length of the unit is approximately 7.25 inches and it weighs approximately 2 ounces.

FIG. 4 shows a sectional view of the housing 20 of the pachymeter 36 with the various components installed. At the rear end of the housing 20 is located a reset switch 50 and a Murata microspeaker 52 is located directly beneath the microprocessor 46 on the opposite side of circuit board 44. There is a pinjack 32 located directly below the printed circuit board 44. This pinjack 32 is for an RS232 interface and is used to send data such as corneal thickness or axial length from the pachymeter or biometric ruler to outside instruments such as a microcomputer, a personal computer or printer.

All elements of the instrument are connected to a multilayered circuit board 44. Mounted off the board are four silver oxide batteries 41. Mounted on the circuit board is the discrete circuitry related to transducer signal processing. Also on the circuit board are connectors to the display 28, the reset button 50, and the RS232 pinjack 32.

The system of the present invention allows for the accurate recording of time between the reception of asynchronous ultrasonic echoes. It is desirable to sample the ultrasonic echoes at high frequency. In the system of the present invention a grey code counter is clocked at a frequency of 40 MHz. The grey code counter is then used to clock a 9-bit counter. After an echo is received, three successive measurement periods, 25 ns apart, sample both the grey code counter and the 9-bit counter. By comparison of the two grey code samples, it can be determined which of the 9-bit samples occur when the 9-bit counter is stable while still allowing for an accuracy of 25 ns. This will be explained in greater detail later.

Figure 5:
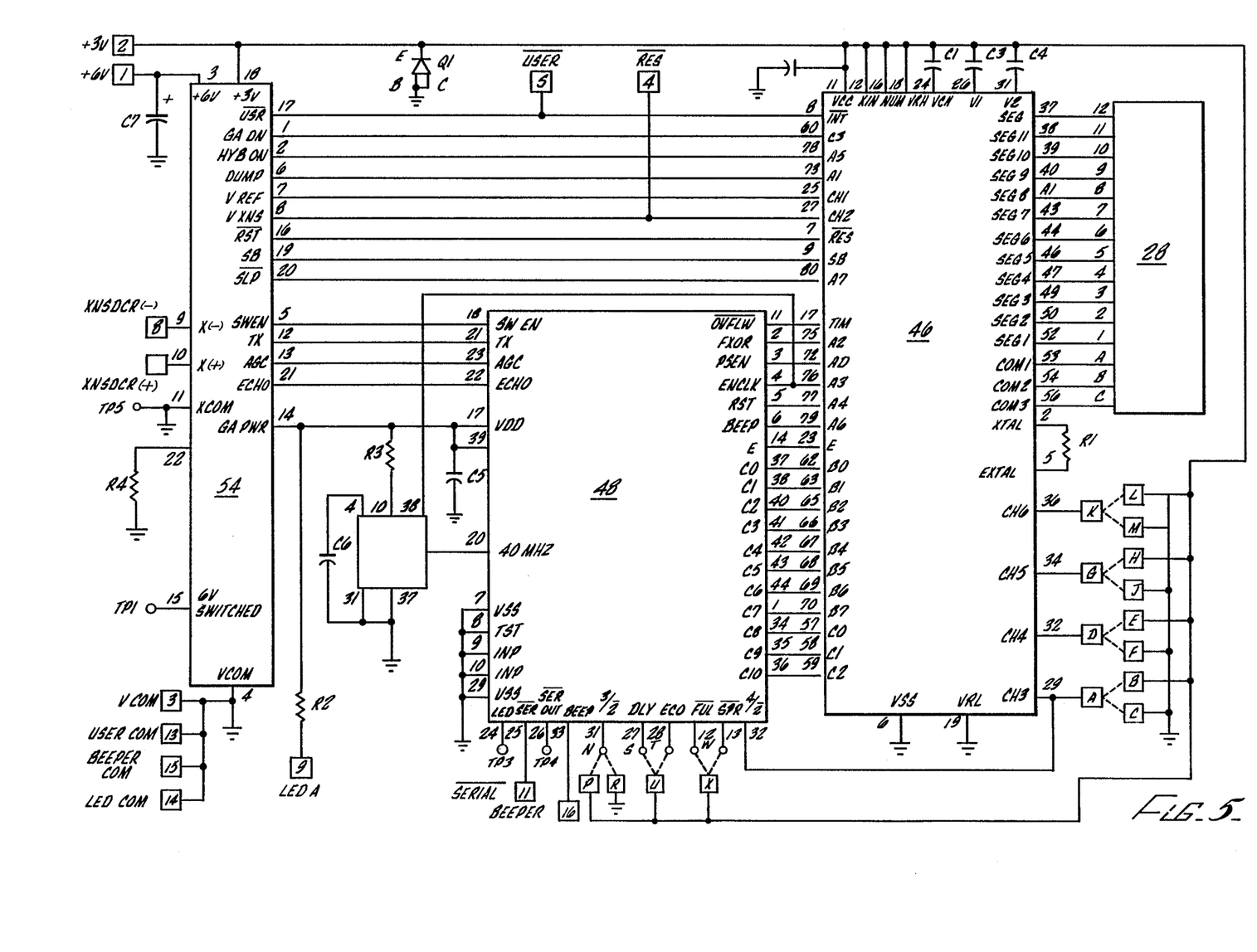
FIG. 5 shows a detailed block diagram of the present system.

FIG. 5 is a detailed block diagram of the present system. This system consists of a hybrid transceiver and signal processor 54, a gate array 48, a microprocessor 46, and a display 28. The hybrid transceiver 54 utilizes several dozen discrete, but miniaturized components. The primary circuit is a multistage amplifier with provisions for rectification of the received echoes. Due to the speed of the 20 MHz transducer, the gate array 48, is necessary to both activate the transducer and also to receive the signal from the transducer. The gate array 48, in turn, processes and sends signals back to the microprocessor 46 at a rate appropriate to that device. As previously stated, one to three excitation pulses are sent to the transducer 22, afterwards the transducer is switched to "listen" mode. This cycle of excitation and reception is performed at a rate of approximately 100 Hz. The initial ultrasonic wave sent through the cornea must be damped electronically to prevent interference with the echoes. The microprocessor keeps track of the leading edges of the received echoes. Once an optimal wave has been identified, then a search begins for the minimum distance between interior and posterior surfaces of the cornea. In other words, a minimum of delay between the time of excitation and the time of echo reception is sought by the microprocessor software. As long as new minimums for corneal thickness are being achieved, processing continues. A barely audible click corresponds to achieving a new minimum. Once there has been no new minimum over a period of 2 to 3 seconds, the eight lowest values which are consecutive are averaged statistically in order to determine the corneal thickness. A beep is then sounded signifying the end of processing. The result is displayed on the liquid crystal display 28, and the measurement number is also sent in ASCII form to an RS232 pinjack 32.

When the instrument is used as a biometric ruler, a 10 MHz transducer is used and the initial ultrasonic wave sent to the cornea is damped both physically and electronically in order to prevent interference with echoes off the anterior corneal surface. The microprocessor, which uses a different program in this mode, keeps track of the minimum amplitudes of the received echoes. If these are above initial threshold level, the threshold is progressively increased until peaks are no longer detected. Sensitivity is then increased by a small amount so that detection occurs at the peak of the signal rather than at the leading edge. These functions are the same as when the 20 MHz transducer is used. The initial algorithm is to search for four peaks in addition to the anterior corneal spike at the level of the transducer head. These four spikes, the anterior and posterior lenticular echoes, the retinal echo, and the scleral echo, constitute an optimal alignment. If, after fifteen seconds, the four peaks have not been detected, then an alternate mode is initiated. In this mode, only three peaks are necessary in order to make a reading. These must include either the anterior or posterior lenticular spike and the retinal spike. The scleral spike becomes optional if both lenticular peaks are identified. If fewer than three peaks are found, no reading is made. If threshold readings are available for the three or more spikes, then an algorithm searches for the longest average distance between the cornea and the posterior pole. This corresponds to the axial length. This algorithm is required because pressure on the cornea from the transducer head can artificially shorten the axial length. A running average of the maximal length is kept under either circumstance, and when the average is stable, a reading is presented to the liquid crystal display 28 (as shown in FIG. 2B), at which time a beep also sounds. During the reading cycle, each time a new reading with a longer axis length is identified, a barely audible click is heard. Once no new maxima occur over a period of two to three seconds, the lowest consecutive values are averaged statistically in order to determine axial length, which corresponds to the beep as mentioned. The reading is accomplished by annunciator lights 56 (FIG. 2B), indicating whether four or three peaks were used to determine the reading. Each of the four noncorneal peaks is identified as a separate annunciator 56. Therefore, the actual pattern of the waveform used to identify axial length is available to the user.

The axial length is not only available as a display on the liquid crystal display, it is also sent in ASCII form to an RS232 pinjack 32 (FIG. 4). Alternatively, the actual waveforms can be transmitted to an oscilloscope.

In the case of aphakia, the anterior and posterior lenticular spikes are not available. Axial length calculation is required for the placement of secondary lens implants with appropriate power. Because it is impossible to align multiple interfaces to ensure axial scan, the reliability of such measurements is less than could be expected in aphakic patients. Therefore, in order to initiate an aphakic mode measurement, the activation button 26 is pressed twice in rapid succession. The patient is then asked to look at LED emitter 40 (FIG. 1B) in the middle of the transducer head 42 (FIG. 1B). Once the retinal and scleral spikes are identified using the thresholding identification algorithms, the maximum length is sought in a manner analogous to the evaluation performed in the aphakic examination. The results are displayed n the display 28, sent to the pinjack 32, and the annunciators 56 corresponding to the retinal and scleral spikes are illuminated on the LCD 28.

Figure 6:
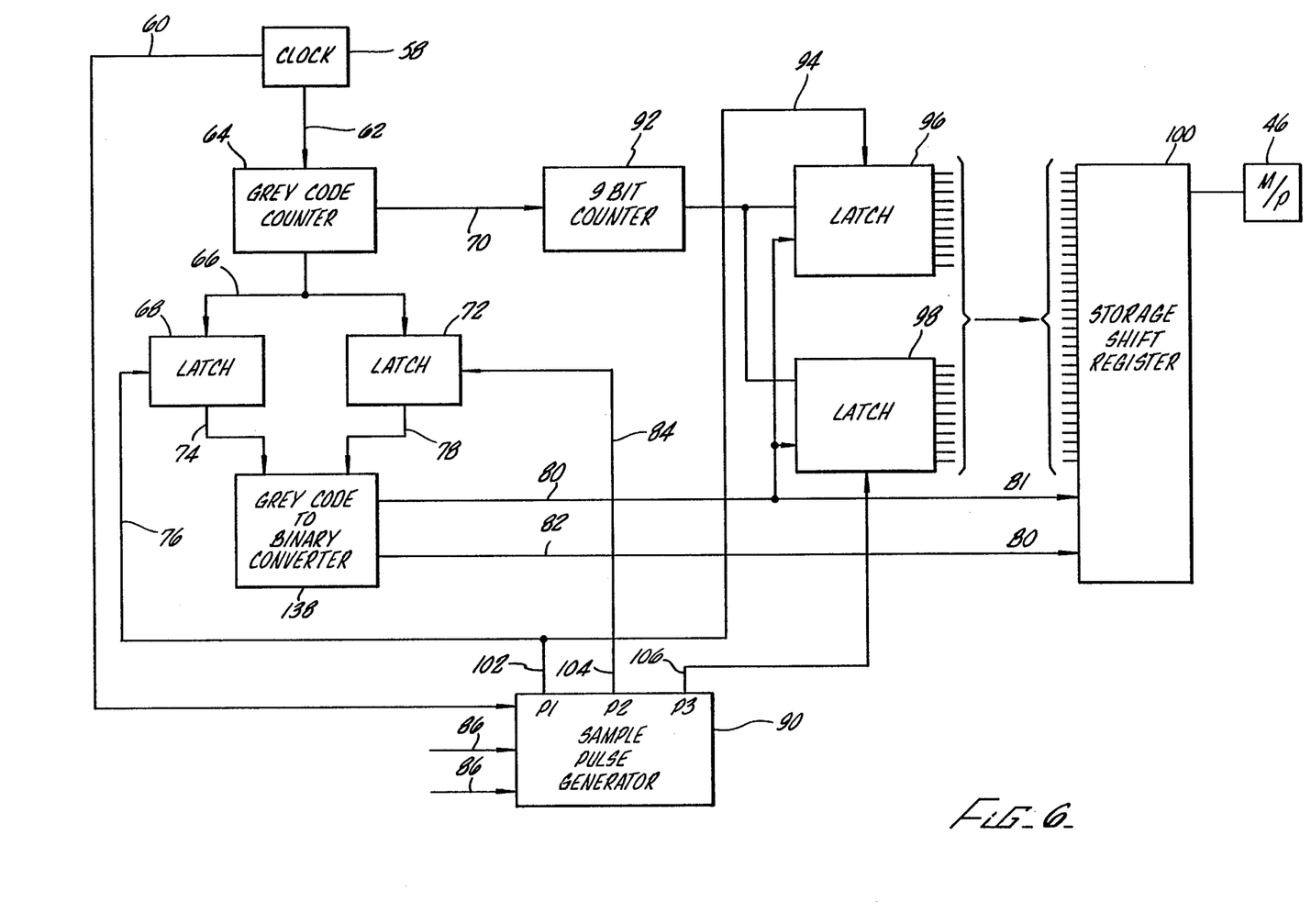
FIG. 6 shows a block diagram of the apparatus for accurately measuring the time between asynchronous events.
Figure 8A:
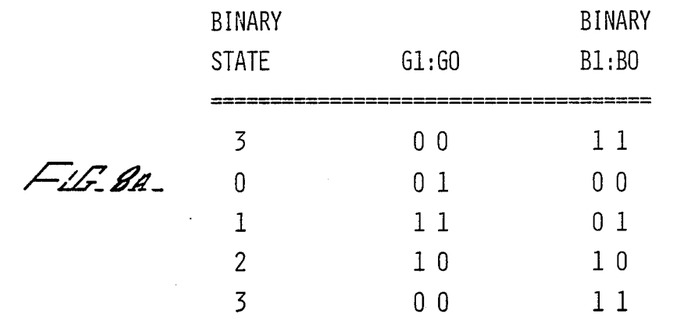
FIG. 8A is a table showing the grey code bit sequence and the corresponding binary outputs and FIG. 8B shows the relation of the binary state of FIG. 8A with 9-bit counter functions.

FIG. 6 is a partial block diagram of the gate array 48. The clock 58 is operating at a frequency of 40 MHz. The grey code counter 64 is clocked at 40 MHz via line 62. The clock 58 is also used to clock the sample pulse generator 90 via the lead 60. The clock 58 and grey code counter 64, as well as a 9-bit counter 92, run continuously and independently of any ultrasonic echoes that are received. When an ultrasonic echo is received on a lead 86, the measurement sequence is initiated. The grey code counter 64 has a continuous output corresponding to the output as shown in FIG. 8A, column 2. As shown in FIG. 8A, the grey code output in sequence goes from 00 to 01 to 11 to 10 and then back to 00 in a continuous fashion. This grey code output is converted to a binary output also as shown in FIG. 8A, column 3. Thus, the grey code output 00 corresponds to the binary output 11 or 3. It is important to note that upon the transition of the grey code output from 00 to 01, a transition of the binary output is from 11, or 3, to 00 or 0. When this transition occurs, a 9-bit counter 92 is advanced by one count. The 9-bit counter 92 counts continuously from 0 to 511 in binary. When the decimal number 511 is reached, the counter wraps around and continues to count from 0 to 511 again, independently of any ultrasonic echoes that are received. An ultrasonic echo, received on line 86, initiates the sampling process. The sample pulse generator 90 generates three sample pulses P1, P2 and P3 which are present on the leads 102, 104 and 106, respectively. The P1 sample pulse occurs 100 ns after an echo is received on lead 86. 25 ns later, sample pulse P2 is generated and 25 ns after that sample pulse P3 is generated. When the sample pulse P1 is generated by sample pulse generator 90, a sample pulse is present on lead 102 which causes latch 68 to sample the output of the grey code counter. Simultaneously a sample pulse is sent to latch 96 which samples and holds the current counter value of 9-bit counter 92. When sample pulse P2 occurs, a sample signal is sent via lead 104 to latch 72 which takes another sample of the current grey code count in the grey code counter 64. When the sample pulse P3 occurs, a sample pulse is present on lead 106 which causes the latch 98 to take another sample of the 9-bit counter 92. At this point the necessary data has been obtained so that the system can determine which sampling of the 9-bit counter 92 has occurred at a time when the 9-bit counter is stable as opposed to being in a state of transition. A better understanding of this operation can be seen by referring to FIG. 7 showing a timing diagram encompassing the previously described operation.

Figure 9:
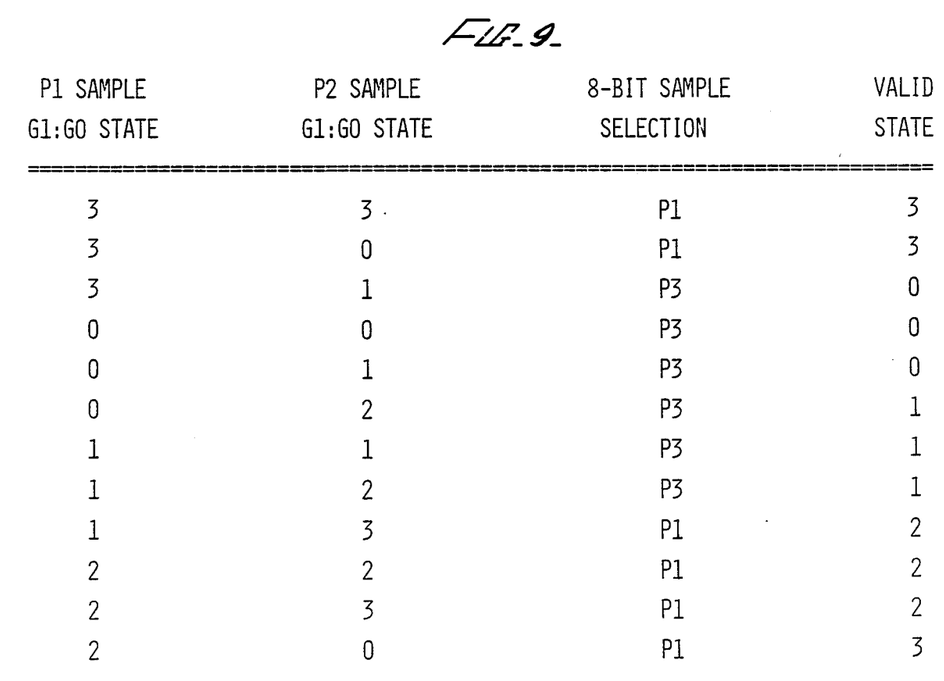
FIG. 9 shows a table listing the binary states of the grey code counter at various P1 and P2 sample periods.

In FIG. 7, waveform 108 is a representation of the signal from the 40 MHz clock 58 of FIG. 6. The waveform 110 represents the least significant bit out of grey code counter 64 and the waveform 112 (G1) represents the other signal (the most significant bit) out of the grey code counter 64. Waveform 114 represents the output out of the 9-bit counter 92. Waveform 116 represents an ultrasonic echo received on lead 86 into sample pulse generator 90. The waveforms 118, 120 and 122 represent the sample pulses P1, P2 and P3 generated in the sample pulse generator (shift register) 90. It should be noted that it is critical that the grey code counter is clocked on the opposite edge of the clock 58 (waveform 108) from the sample pulse generator 90 to avoid metastability in the grey code samples. Dotted line 130 of FIG. 9 shows that the waveform 110 goes high. This transition causes the 9-bit counter, waveform 114, to start its transition to its next count. Note that the rising edge of waveform 116, the received echo, occurs, in this example, during a transition of the 9-bit counter 92. Since there is a built-in delay of 100 ns between the leading edge of the echo 68 and the leading edge of the sample pulse P1, 118, this delay can be eliminated because it is present for each echo that is sampled. At a dotted line 124, the grey code counter 64 is sampled as well as the 9-bit counter 92. As can be seen, the grey code counter has a value of 01 and the 9-bit counter 92 is in a state of transition. Therefore, the 9-bit counter number stored in latch 96 has been recorded during a state of transition. In the next sample, P2 is taken as shown at a dotted line 126, and the grey code is in the 11 state which is equivalent to a binary count of 1 as shown in Table 8A. Therefore, the grey code has transitioned between a count of 0 to a count of 1, FIG. 8A, column 1. Referring to FIG. 9, this indicates that the valid state is 0 and that the 9-bit sample taken as sample pulse P3, represented by dotted line 128, did not occur during a transition state of the 9-bit counter 92. Thus, the measurement taken at P3, represented by the dotted line 128, is the valid measurement of the sample of 9-bit counter 92.

At this time, it should be noted that there are only certain grey code counter sequences that are possible when it has been sampled at a time period P1 and P2. For instance, the samples at times P1 and P2 could fall at a time when the grey code counter is in a state of transition. Under these circumstances three things can happen; the successive grey code samples at P1 and P2 will read 00 and 00, they will read 00 and 01 or, for instance, 00 and 11 wherein the 01 count has been skipped. Since the grey code counter makes a transition every 25 ns and because the time between the samples P1 and P2 is 25 ns, it is not possible for the successive P1 and P2 readings to skip more than one count of the grey code. A further explanation of this operation is shown in FIG. 9. The output state of the grey code counter is converted to a binary output and for ease of reference we will use the decimal number relating to that binary output. As shown in column 1, if the first P1 sample results in a binary output of 3 and the following P2 sample results in the same binary output of 3, then the first sample of the 9-bit counter is valid. Similarly, if the first P1 sample results in a binary output of 3 and the P2 sample results in a binary output of 0, then there has been one transition of the grey code counter and again the P1 reading of the 9-bit counter is valid. However, if the two successive samplings of the grey code counter reveals that a count of the grey code counter has been skipped, such as a P1 reading of 3 and a P2 reading of 1, then the valid state is 0. However, when the valid state is 0, there has been a grey code counter transition which has clocked the next count of the 9-bit counter. Since there is a state of transition immediately after that clock pule, then the P3 sample of the 9-bit counter 92 is valid as opposed to the P1 sample.

Figure 8B:
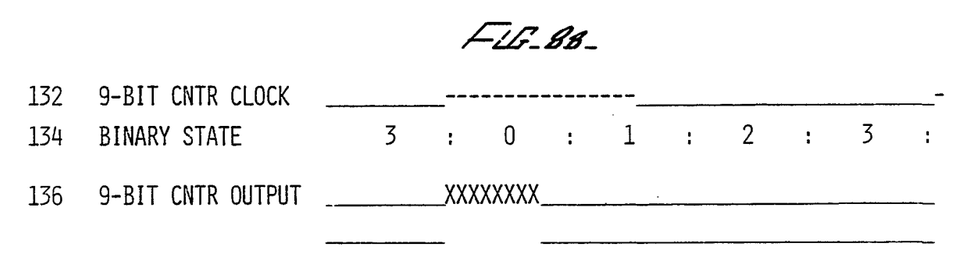

Referring to FIG. 8B, waveform 132 shows a transition of the 9-bit counter which occurs at the 3 to 0 transition of the grey code counter 64 as shown in the line 134. Immediately after this transition, the output of the 9-bit counter 92 is in a state of transition as represented by the x's of the line 136. Therefore, as shown in FIG. 9, anytime the valid state of the grey code counter is 0 or 1, the 9-bit counter 92 has a valid sample during the P3 sample, and anytime the valid state is 2 or 3, then the P1 sample of the 9-bit counter is valid. Also, it should be noted that the binary output of the grey code counter represents the two least significant bits of the 11-bit counter which corresponds to the 9 bits from the 9-bit counter 92 and the two binary outputs of the grey code counter 64 as converted by binary converter 138 of FIG. 6. Since the grey code counter 64 clocks the 9-bit counter on the 3 to 0 transition of the grey code counter, FIG. 8B, the first two bits of the grey code converter can be used as part of the 11-bit counter after the grey code counter output has been converted to binary by converter 138.

When the activation switch has not been depressed for two minutes, the microprocessor 46 and transducer elements are automatically turned off in order to reduce power consumption and the battery life. A small discrete circuit performs this function and also responds to depression of the activation button by activating the electronic elements and the transducer.

Thus, through the system of the present invention, a high speed and highly accurate apparatus for correlating asynchronous echoes to a high speed sampling circuit has been achieved. This allows for greater sensitivity, resolution, accuracy and range when compared to other systems of ophthalmic pachymeters currently available.

While the preferred embodiment of the system of the present invention has been illustrated and described, certain modifications and alternatives will be apparent to those skilled in the art and the present disclosure is intended to include such modifications and alternatives within the scope of the appended claims.

What is claimed is:

1. An asynchronous signal detection system in which asynchronous signals are detected and correlated to synchronous signals comprising sample pulse means for receiving asynchronous signals and generating a plurality of sample pulses, counter means for counting in a continuous manner, grey code counter means for counting in a continuous manner and for clocking said counter means, latch means comprising a first latch, a second latch, a third latch and a fourth latch wherein said latch means is connected to said sample means and wherein said first and second latches are connected to said grey code counter means and said third and fourth latches are connected to said counter means and wherein said sample pulses are adapted to cause said first and second latches to latch data from said grey code counter means and said third and fourth latches are adapted to latch data from said counter means, and converter means for receiving and converting data from said first and second latches for controlling said third and fourth latches.

2. A system as in claim 1 including shift register means connected to said third and fourth latches for storing data transferred from said third and fourth latches, microprocessor means connected to said shift register means for receiving data from said shift register means and converting said data from said shift register means to thickness data, and display means, connected t o said microprocessor means for digitally displaying said thickness data.

3. A system as in claim 2 including transducer means for transmitting pulses and receiving asynchronous pulses and converting said asynchronous pulses to asynchronous signals, and transmitter/receiver means connected to said transducer means and said sample pulse means for receiving and processing said asynchronous signals from said transducer means and providing said asynchronous signals to said sample pulse means.

* * * * *